US011992706B2

(12) United States Patent
Wang et al.

(10) Patent No.: US 11,992,706 B2
(45) Date of Patent: May 28, 2024

(54) SIMULATION PHANTOM

(71) Applicant: OUR UNITED CORPORATION, Xi'an (CN)

(72) Inventors: Zhongya Wang, Xi'an (CN); Hao Yan, Xi'an (CN); Jiuliang Li, Xi'an (CN)

(73) Assignee: OUR UNITED CORPORATION, Xi'an (CN)

(*) Notice: Subject to any disclaimer, the term of this patent is extended or adjusted under 35 U.S.C. 154(b) by 333 days.

(21) Appl. No.: 17/624,515

(22) PCT Filed: Jun. 30, 2020

(86) PCT No.: PCT/CN2020/099346
§ 371 (c)(1),
(2) Date: Jan. 3, 2022

(87) PCT Pub. No.: WO2021/000861
PCT Pub. Date: Jan. 7, 2021

(65) Prior Publication Data

US 2022/0362578 A1 Nov. 17, 2022

(30) Foreign Application Priority Data

Jul. 2, 2019 (CN) ......................... 201910590042.8
Jul. 2, 2019 (CN) ......................... 201921022791.2

(51) Int. Cl.
*A61N 5/10* (2006.01)
*A61B 6/58* (2024.01)

(52) U.S. Cl.
CPC ............ *A61N 5/1039* (2013.01); *A61B 6/583* (2013.01)

(58) Field of Classification Search
CPC .......... A61N 5/1039; A61N 2005/1076; A61N 5/1075; A61B 6/583; A61B 5/0035;
(Continued)

(56) References Cited

U.S. PATENT DOCUMENTS 5,034,969 A * 7/1991 Ozaki .................... A61B 6/583 378/18
5,368,030 A 11/1994 Zinreich et al.
(Continued)

FOREIGN PATENT DOCUMENTS

CN 102178526 A 9/2011
CN 102824216 A 12/2012
(Continued)

OTHER PUBLICATIONS

International Search Report of the International Searching Authority for State Intellectual Property Office of the People's Republic of China in PCT application No. PCT/CN2020/099346 dated Oct. 12, 2020, which is an international application corresponding to this U.S. application.

*Primary Examiner* — Kiho Kim
(74) *Attorney, Agent, or Firm* — Kolitch Romano Dascenzo Gates LLC

(57) ABSTRACT

Provided is a simulation phantom including a simulated target volume and a simulated normal tissue encasing the simulated target volume, wherein the simulated target volume and a portion of the simulated normal tissue abutting the simulated target volume have a first characteristic to enable the simulation phantom to be imaged on a first imaging device, and the simulated target volume and the portion of the simulated normal tissue abutting the simulated target volume further have a second characteristic to enable the simulation phantom to be imaged on a second imaging device different from the first imaging device.

19 Claims, 4 Drawing Sheets

(58) Field of Classification Search
CPC ....... A61B 5/0036; A61B 5/055; A61B 6/032; A61B 6/4085; A61B 6/4417; A61B 6/5247; A61B 8/587; G01R 33/4812; G01R 33/58
See application file for complete search history.

(56) References Cited

U.S. PATENT DOCUMENTS

| | | | |
|---|---|---|---|
| 5,469,847 | A | 11/1995 | Zinreich et al. |
| 2015/0011861 | A1 | 1/2015 | Rahmer et al. |

FOREIGN PATENT DOCUMENTS

| | | | |
|---|---|---|---|
| CN | 104105456 | A | 10/2014 |
| CN | 106901765 | A | 6/2017 |
| CN | 106923854 | A | 7/2017 |

* cited by examiner

SIMULATION PHANTOM

CROSS-REFERENCE TO RELATED APPLICATION

This application is a US national stage of PCT international patent application PCT/CN2020/099346 filed on Jun. 30, 2020, which claims priority to Chinese Patent Application No. 201910590042.8, filed on Jul. 2, 2019 and entitled "SIMULATION PHANTOM", and Chinese Patent Application No. 201921022791.2, filed on Jul. 2, 2019 and entitled "SIMULATION PHANTOM", the disclosures of which are incorporated herein by reference in their entireties.

TECHNICAL FIELD

The present disclosure relates to the field of radiotherapy technologies, in particular to a simulation phantom.

BACKGROUND

Radiation therapy, referred to as radiotherapy, is a treatment method for killing cancer cells by irradiating tumors with high-energy rays (such as X-rays or γ-rays) or energetic particles (such as protons or heavy ions). In order to ensure the accuracy of radiotherapy, the entire radiotherapy process shall be simulated, prior to the treatment of a patient, by using a phantom instead of the patient, to verify the accuracy of the treatment plan or radiotherapy device.

SUMMARY

Embodiments of the present disclosure provide a simulation phantom. The simulation phantom includes the following technical solutions.

A simulation phantom includes a simulation phantom, comprising a simulated target volume and a simulated normal tissue encasing the simulated target volume, wherein the simulated target volume and a portion of the simulated normal tissue abutting the simulated target volume have a first characteristic to enable the simulation phantom to be imaged on a first imaging device, and the simulated target volume and the portion of the simulated normal tissue abutting the simulated target volume further have a second characteristic to enable the simulation phantom to be imaged on a second imaging device different from the first imaging device.

Optionally, the first characteristic indicates a difference in CT value and the first imaging device is a CT imaging device; and the second characteristic indicates a difference in hydrogen-containing density and the second imaging device is a magnetic resonance imaging device.

Optionally, the simulation phantom further includes: a cassette for accommodating the simulated target volume, wherein a cassette recess is provided in the simulated normal tissue at a position corresponding to the cassette, the cassette fits and is capable of being housed in the cassette recess, and is detachably connected with the cassette recess, and the simulated target volume and the cassette have the first characteristic and the second characteristic.

Optionally, the simulated normal tissue includes a first body and a second body that are detachably connected to each other, and the cassette is capable of being housed in or removed from the cassette recess by detaching the first body and the second body.

Optionally, the simulated target volume is in a sphere shape.

Optionally, a plurality of precisely-marked points for positioning the simulation phantom are provided at an outer surface of the simulated normal tissue.

Optionally, in a case that the simulation phantom is a simulated head phantom, the plurality of precisely-marked points comprise a first precisely-marked point, a second precisely-marked point and a third precisely-marked point, wherein the first precisely-marked point is disposed at a forehead of the simulated head phantom; the second precisely-marked point and the third precisely-marked point are respectively disposed at opposite sides of the forehead of the simulated head phantom; and a center point of the simulated target volume coincides with an intersection between a line connecting the second precisely-marked point and the third precisely-marked point, and a line perpendicular to the connecting line and passing through the first precisely-marked point.

Optionally, the precisely-marked points and the outer surface of the simulated normal tissue at least have the first characteristic or the second characteristic.

Optionally, a plurality of marked points are provided inside the simulated normal tissue, and the plurality of marked points and portions of the simulated normal tissue abutting the marked points at least have the first characteristic or the second characteristic.

Optionally, in a case that the simulation phantom is a simulated head phantom, the plurality of marked points are disposed in a simulated soft tissue of a forehead of the simulated head phantom.

Optionally, a film housing groove for housing a film is provided within the cassette.

Optionally, the cassette includes a first cassette and a second cassette opposite to and detachably connected to each other, and the film housing groove is formed between opposite surfaces of the first cassette and the second cassette.

Optionally, the first cassette and the second cassette are detachably connected to each other via a locating pin and locating hole that are mutually fitted.

Optionally, a spherical hollow cavity is provided in the center of the simulated target volume, and a spherical point of the spherical hollow cavity coincides with a center point of the simulated target volume.

Optionally, in a case that the simulation phantom is a simulated head phantom, the cassette is disposed between a back surface and a front surface of the simulated head phantom.

Optionally, the cassette is in a cuboid or cube shape.

Optionally, the simulation phantom is a simulated head phantom, a simulated head-neck phantom or a simulated body phantom.

Optionally, in a case that the simulation phantom is the simulated head phantom or the simulated head-neck phantom, the simulated normal tissue comprises a simulated skull, a simulated soft tissue filled within the simulated skull, and a simulated skin disposed outside the simulated skull, and wherein the simulated target volume is disposed within the simulated soft tissue, and the simulated skull, the simulated soft tissue, and the simulated skin at least have the first characteristic or the second characteristic.

Optionally, a simulated target volume driving device for driving the simulated target volume to move along a predetermined trajectory at a predetermined frequency.

BRIEF DESCRIPTION OF THE DRAWINGS

For clearer descriptions of the technical solutions in the embodiments of the present disclosure or the prior art, the following briefly introduces the accompanying drawings required for describing the embodiments or the prior art. Apparently, the accompanying drawings in the following description show merely some embodiments of the present disclosure, and persons of ordinary skill in the art may still derive other drawings from these accompanying drawings without creative efforts.

DETAILED DESCRIPTION

Figure 1:
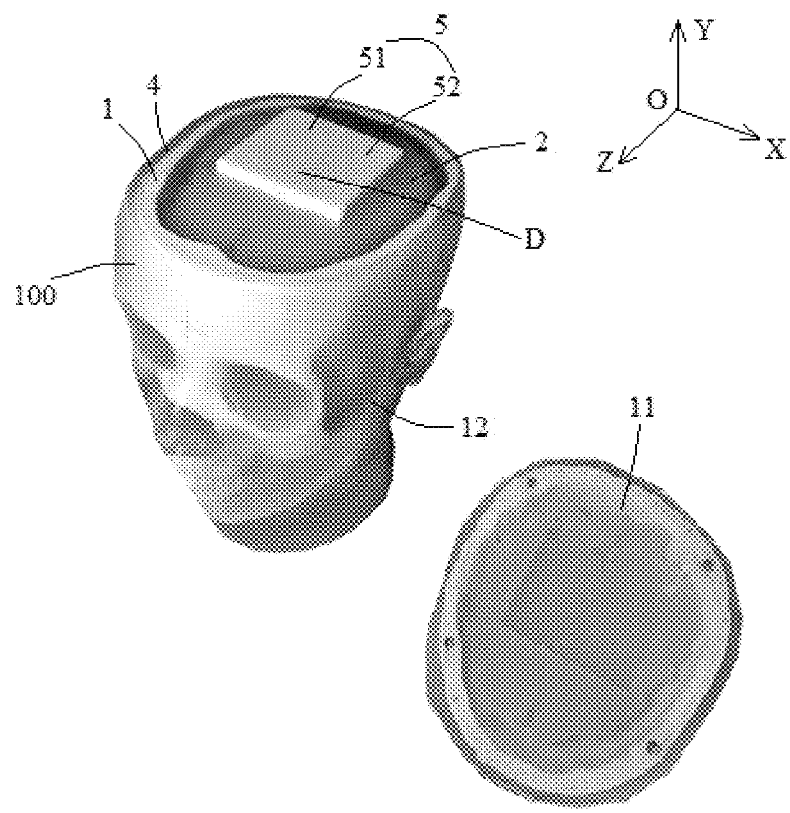
FIG. 1 is a schematic diagram showing a first body and a second body, in a detached state, of a simulation phantom according to some embodiments of the present disclosure.

The technical solutions of some embodiments of the present disclosure will be described clearly and completely below in combination with the accompanying drawings illustrating these embodiments of the present disclosure. It is obvious that the described embodiments are only a part of embodiments of the present disclosure, not all embodiments of the present disclosure. All other embodiments, which can be obtained by those of ordinary skills in the art based on the embodiments of the present disclosure without any creative work, shall fall within the protection scope of the present disclosure.

In the description of the present disclosure, it should be understood that, the orientation or position relationships indicated by the terms "center", "on", "below", "front", "rear", "left", "right", "vertical", "horizontal", "top", "bottom", "inside", "outside", etc. are based on the orientation or position relationships as shown in the drawings, which are used for ease of the description of the present disclosure and simplifying the description only, rather than for indicating or implying that the indicated device or element must be in a particular orientation or be constructed and operated in a particular orientation. Therefore, these terms should not be understood as a limitation to the present disclosure.

In addition, the terms such as "first" and "second" are merely for a descriptive purpose, and should not be understood as indicating or implying a relative importance, or implicitly indicating the number of the technical features as indicated. Hence, the feature defined by "first" or "second" can explicitly or implicitly includes one or more said feature. In the description of the present disclosure, "a plurality of" means two or more in number, unless otherwise stated.

In the description of the present disclosure, it should be noted that, unless otherwise specified and defined, the terms "mount", "connected with", "connected to" or the like should be comprehended in a broad sense. For example, these terms may be comprehended as that the components are fixedly connected, detachably connected or integrally connected; or that the components are directly connected, or indirectly connected via an intermediate object, or the components have an internal communication therebetween. The specific meanings of the foregoing terms in the present disclosure can be understood by those skilled in the art according to specific circumstances.

In the simulation process by using a simulation phantom to verify the accuracy of the treatment plan or radiotherapy device, the simulation phantom needs to be imaged. However, the simulation phantom in the related art can only be imaged on one imaging device, and in order to meet different needs, it is necessary to prepare a plurality of phantoms that are suitable for being imaged on different imaging devices, which not only leads to increased costs but also makes it inconvenient for storage and sorting.

Figure 2:
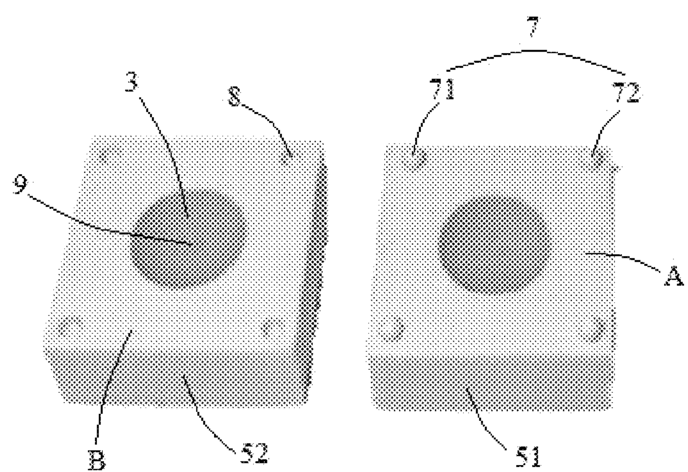
FIG. 2 is a schematic diagram showing a cassette of a simulation phantom, being opened, according to some embodiments of the present disclosure.
Figure 3:
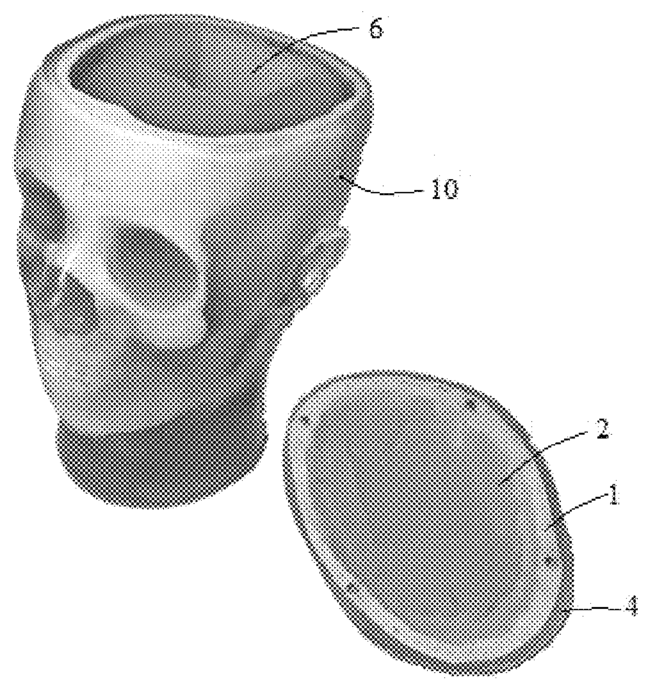
FIG. 3 is a schematic diagram showing a first body and a second body, in a detached state with the cassette being removed, of a simulation phantom according to some embodiments of the present disclosure.

As shown in FIGS. 1 to 3, the simulation phantom in these embodiments include a simulated target volume 3 and a simulated normal tissue 100 that encases the simulated target volume 3. The simulated normal tissue 100 may be a soft tissue or a bone, or may be both soft tissue and bone. The simulated target volume 3 and the portion of the simulated normal tissue 100 abutting the simulated target volume 3 have a first characteristic to enable the simulation phantom to be imaged on a first imaging device; and the simulated target volume 3 and the portion of the simulated normal tissue 100 abutting the simulated target volume 3 further have a second characteristic to enable the simulation phantom to be imaged on a second imaging device that is different from the first imaging device.

In the simulation phantom according to the embodiments of the present disclosure, as the simulated target volume 3 and the portion of the simulated normal tissue 100 abutting the simulated target volume 3 have a first characteristic to enable the simulation phantom to be imaged on a first imaging device, and the simulated target volume 3 and the portion of the simulated normal tissue 100 abutting the simulated target volume 3 further have a second characteristic to enable the simulation phantom to be imaged on a second imaging device different from the first imaging device, the simulation phantom can be imaged on at least two different imaging devices, which can reduce the number of simulation phantoms that requires to be prepared, thereby not only reducing the costs but also facilitating the storage and sorting.

The first imaging device and the second imaging device may each be any one of a CT imaging device, a magnetic resonance imaging device, an ultrasonic imaging device or other imaging devices, as long as the first imaging device and the second imaging device are different. Exemplarily, the first characteristic may refer to a difference in CT value. In order words, the simulated target volume 3 and the portion of the simulated normal tissue 100 abutting the simulated target volume 3 have different CT values, such that the simulation phantom can be imaged on a CT imaging device (that is, the first imaging device is a CT imaging device). The second characteristic may refer to a difference in hydrogen-containing density. In order words, the simulated target volume 3 and the portion of the simulated normal tissue 100 abutting the simulated target volume 3 may have different hydrogen-containing densities (in this case, the simulated target volume 3 and the portion of the simulated normal tissue 100 abutting the simulated target volume 3 shall be made of a hydrogen-containing material, which may be polymethyl methacrylate, acrylic acid or agarose gel, etc.), such that the simulation phantom may be imaged on a magnetic resonance imaging device (that is, the second imaging device is a magnetic resonance imaging device). The second characteristic may otherwise refer to difference in acoustic impedance and acoustic attenuation characteristic. In other words, the simulated target volume 3 and the portion of the simulated normal tissue 100 abutting the simulated target volume 3 may have different acoustic impedances and acoustic attenuation characteristics, such that the simulation phantom can be imaged on an ultrasonic imaging device (that is, the second imaging device is an ultrasonic imaging device). Of course, the simulation phantom may also be imaged on an imaging device other than the first imaging device and the second imaging device, and may for example be imaged on a third imaging device.

Optionally, the simulation phantom further includes a cassette 5 for accommodating the simulated target volume 3. A cassette recess 6 is further provided in the simulated normal tissue 100 at a position corresponding to the cassette 5, and the cassette 5 fits and is capable of being housed in the cassette recess 6 and is detachably connected to the cassette recess 6. The simulated target volume 3 and the cassette 5 have the first characteristic and the second characteristic. Thus, a plurality of cassettes 5 each having a different-shaped simulated target volume 3 may be prepared, and when it is necessary to change to a simulated target volume 3 having a different shape, a corresponding cassette 5 can be selected and mounted into the cassette recess 6 according to needs.

Figure 4:
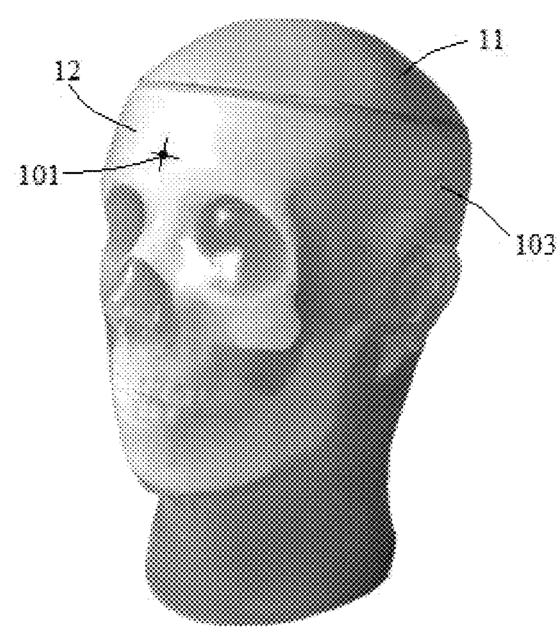
FIG. 4 is an overall schematic diagram of a simulation phantom according to some embodiments of the present disclosure.
Figure 5:
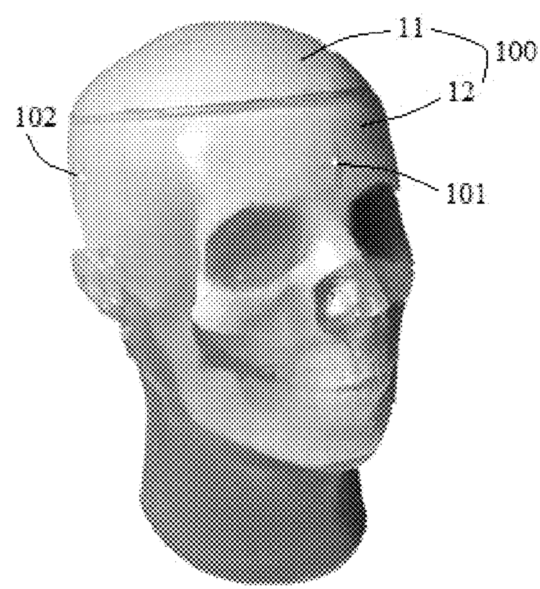
FIG. 5 is an overall schematic diagram of a simulation phantom according to some embodiments of the present disclosure viewed from another angle.

Referring to FIGS. 4-5, in order to mount the cassette 5 into or remove it from the cassette recess 6 conveniently, the simulated normal tissue 100 in these embodiments may include a first body 11 and a second body 12 that are detachably connected to each other. By detaching the first body 11 and the second body 12, the cassette 5 can be housed in or removed from the cassette recess 6. Then, the first body 11 and the second body 12 are connected together to enable the simulation phantom to be an integral structure.

Optionally, the simulated target volume 3 is in a sphere shape, which makes it easier to outline the spherical target volume and determine the center of the sphere while developing a treatment plan, and thereby facilitates the setting of the target point.

In order to determine the cumulative errors of the radiotherapy device (i.e., to determine the comprehensive positioning accuracy), after imaging the simulation phantom on the first imaging device or the second imaging device and developing the treatment plan, it is necessary to position the simulation phantom before performing "radiotherapy" on the simulation phantom. For this purpose, a plurality of precisely-marked points 10 are provided at the outer surface of the simulated normal tissue 100 in these embodiments (referring to FIG. 3 for example). Thus, when a laser light is adopted for the positioning, the treatment bed can be controlled to move to enable the precisely-marked points 10 at the outer surface of the simulated normal tissue 100 to coincide with the crosshairs projected by the laser light, such that an initial positioning of the simulation phantom can be achieved.

Referring to FIGS. 1 to 5, the simulation phantom is a simulated head phantom, and the precisely-marked points 10 include a first precisely-marked point 101, a second precisely-marked point 102, and a third precisely-marked point 103. The first precisely-marked point 101 is disposed at the forehead of the simulated head body; the second precisely-marked point 102 and the third precisely-marked point 103 are respectively disposed at opposite positions at two sides of the forehead of the simulated head body; and a center point of the simulated target volume 3 coincides with an intersection between a line connecting the second precisely-marked point 102 and the third precisely-marked point 103, and a line perpendicular to the connecting line and passing through the first precisely-marked point 101. In these embodiments, the positioning of the simulated head phantom is achieved by configuring the three precisely-marked points 10 to coincide with the crosshairs projected by the laser. Compared with the use of more precisely-marked points 10, these embodiments provide a simpler configuration under the premise of ensuring the positioning function.

After completing the initial positioning of the simulation phantom with the laser light, a registration (e.g., an image-guided registration) on the image formed by an imaging apparatus (e.g., a CBCT) with the image formed by the first imaging device or the second imaging device can be further performed. Then, the position of the simulation phantom can be adjusted based on the registration result to achieve a more accurate positioning of the simulation phantom.

Figure 6:
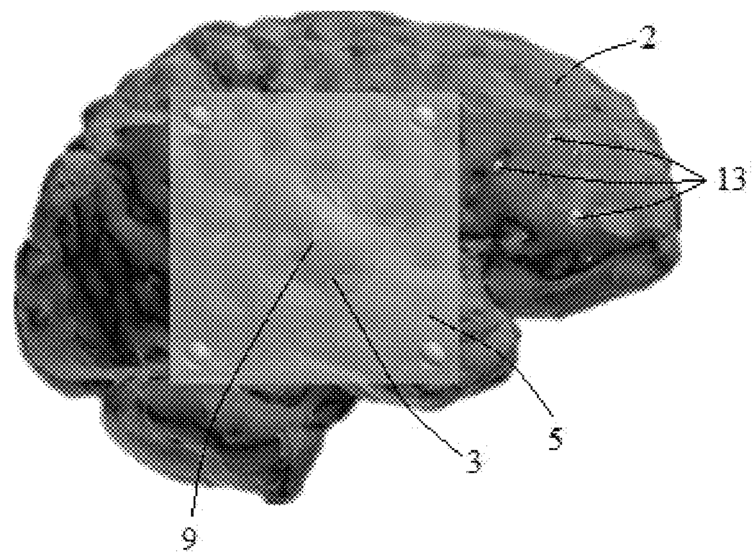
FIG. 6 is a schematic diagram showing marked points in a simulation phantom according to some embodiments of the present disclosure.

To improve the accuracy of the registration, as shown in FIG. 6, a plurality of marked points 13 may further be provided in the simulated normal tissue 100 in these embodiments. The plurality of marked points 13 and the portions of the simulated normal tissue 100 abutting the marked points 13 at least have a first characteristic or a second characteristic, such that after the plurality of marked points 13 are imaged on the first imaging device or the second imaging device, and the image of the plurality of marked points 13 can be distinguished from the image of the portions of the simulated normal tissue 100 abutting the marked points 13 on the first imaging device or the second imaging device. The registration in such registration process can be performed by using a plurality of marked points 13. In addition, the plurality of marked points 13 can also assist in verifying the accuracy of the registration.

It should be noted here that the precisely-marked points 10 and the outer surface of the simulated normal tissue 100 at least have the first characteristic or the second characteristic, so that the image of the precisely-marked points 10 and the image of the outer surface of the simulation phantom can be distinguished from each other on the first imaging device and the second imaging device, which can also assist in verifying the accuracy of the registration.

In a case that the simulation phantom is a simulated head phantom, referring to FIG. 6, the plurality of marked points 13 are disposed in the simulated soft tissue 2 of the forehead of the simulated head phantom, which not only can ensure the assisted verification on the accuracy of the registration, but also can simplify the configuration by avoiding disposing too many marked points 13.

Optionally, the plurality of marked points 13 may be of a rigid substance and may for example be made of a simulated skull-like material. The plurality of marked points 13 may be spheres of different sizes.

Referring to FIGS. 1 to 3, a film housing groove D for housing a film may further be provided within the cassette 5 in these embodiments. Whether an actual beam of an irradiated device can accurately irradiate on the target point can be verified by utilizing the deviation between a focal spot on the film formed by the beam and a preset point, and a comprehensive positioning accuracy can also be reflected by the deviation.

To avoid influencing the accuracy of positioning due to the insertion of the film, the film can be placed in the film housing groove D within the cassette 5 before the positioning process.

Optionally, when it is determined that the registration result has met the preset condition after the image-guided verification, the treatment plan may be initiated, and an irradiation is performed on the target portion in the simulated target volume. In some examples, a film is placed in an XOY plane, and a central axis of the beams is perpendicular to the XOY plane where the film is disposed. After the irradiation, the film is removed, and the position of the focal spot formed on the film and the position of the preset point are analyzed, to determine the deviation of the center point of the focal spot from the preset point in X and Y directions. Similarly, a film is placed in a YOZ plane, and the central axis of the beams is perpendicular to the YOZ plane where the film is disposed, to determine the deviation of the center point of the focal spot from the preset point in Y and Z directions. Finally, the deviations of the center point of the focal spot from the preset point in the X, Y and Z directions can be determined from the two deviations, so that whether the actual beams are capable of accurately irradiating on the target point can be verified, thereby reflecting the cumulative errors of the radiotherapy device (i.e., determining the comprehensive positioning accuracy).

It should be noted here that the preset point is configured to indicate the center point of the simulated target volume, and after the positioning is completed, the preset point should coincide with the isocenter of the machine.

It should also be noted that, in the above discussion, it is merely an example to place one film in the XOY plane and then another film in the YOZ plane. It is also possible to place one film in the YOZ plane and then another film in the XOY plane.

Referring to FIG. 2, the cassette 5 includes a first cassette 51 and a second cassette 52 opposite to and detachably connected to each other, and a film housing groove D is formed between the opposite surfaces A and B of the first cassette 51 and the second cassette 52. That is, the surface A of the first cassette 51 and the surface B of the second cassette 52 are configured to clamp the film. In this way, to verify whether the actual beams can accurately irradiate on the target point. The film may be first placed between the surface A of the first cassette 51 and the surface B of the second cassette 52, and then the irradiation is initiated. After the irradiation is completed, another film is placed between the surface A of the first cassette 51 and the surface B of the second cassette 52, the cassette 5 is rotated to cause the second film to have a different orientation with the previous film, and then the irradiation is initiated. Compared with other cassettes of different structures, the cassette 5 of these embodiments has a larger space for housing the film when it is opened, which facilitates the loading and unloading of the film; and the structure of the cassette 5 is simpler, which makes it more convenient to process.

There are various manners for detachably connecting the first cassette 51 and the second cassette 52. As exemplified in these embodiments, the first cassette 51 and the second cassette 52 may be detachably connected to each other via a locating pin 7 and a locating hole 8 that are mutually cooperated. Referring to FIG. 2, each corner of surface A of the first cassette 51 opposite to the second cassette 52 is provided with a locating pin 7, and each corner of surface B of the second cassette 52 opposite to the first cassette 51 is provided with a locating hole 8; and the plurality of locating pins 7 and the plurality of locating holes 8 are cooperated with each other in a one-to-one correspondence, which enables the first cassette 51 to be engaged with the second cassette 52. Compared with other fashions for realizing the detachable connection, the configuration provided in these embodiments is simple in structure and can be easily detached. In addition, by setting the distance of one locating pin 71 from the edges of the first cassette 51 as being different from that of any other locating pin 72 from the edges of the first cassette 51, the orientation of the film can be easily determined.

In order to make it convenient to determine whether the center point of the focal spot deviates from the preset point, a spherical hollow cavity 9 may be provided in the center of the simulated target volume 3 in these embodiments, and a spherical point of the spherical hollow cavity 9 may coincide with a center point of the simulated target volume 3. In this way, when the first cassette 51 and the second cassette 52 are detached from each other after the irradiation, whether the center point of the focal spot deviates from the spherical center of the spherical hollow cavity 9 can be clearly observed from the film stuck to the first cassette 51 or the second cassette 52, and therefore it is more convenient to determine whether the center point of the focal spot deviates from the preset point.

Figure 7:
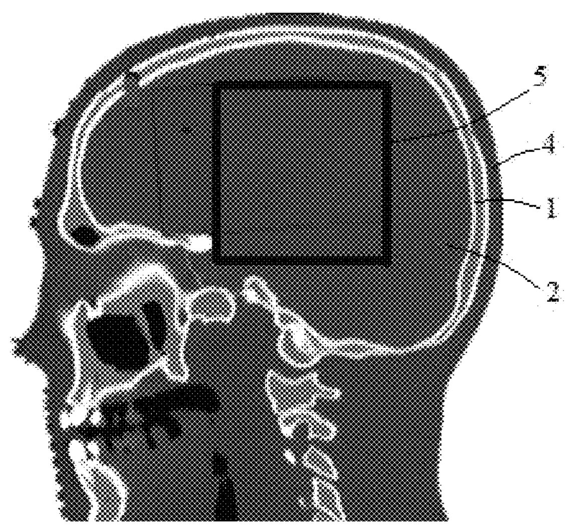
FIG. 7 is a schematic diagram showing a specific position of a cassette in a simulation phantom according to some embodiments of the present disclosure.
Figure 8:
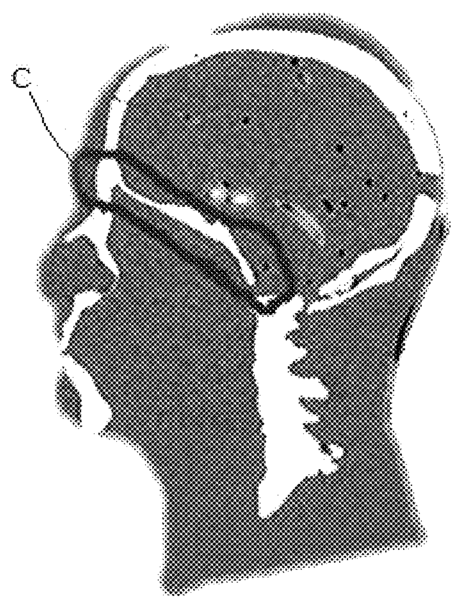
FIG. 8 is a schematic diagram showing the positions that shall be avoided by a cassette in a simulation phantom according to some embodiments of the present disclosure.

Referring to FIGS. 7 and 8, the simulation phantom is a simulated head phantom, and the cassette 5 is preferably disposed between a back surface and a front surface of the simulated head phantom, such that skeletal information from the orbit portion to the spine portion (as marked by C) is covered to the least extent, so that the CT images and nuclear magnetic images can provide more comprehensive information.

The cassette 5 is preferably in a cuboid or cube shape, and the cassette recess 6 in the simulated normal tissue 100 is in a cuboid or cube shape accordingly. When the cassette 5 is rotated to another orientation to irradiate the second film, the inner surface of the cassette recess 6 can limit the cassette 5 and make it maintain that orientation. Compared with the cassettes 5 in other shapes (such as cylinder or sphere, etc.), these embodiments do not need to provide a position-limiting structure for limiting the position of the cassette 5, which facilitates the processing of the simulation phantom.

Optionally, the simulation phantom may be a simulated head phantom, a simulated head-neck phantom or a simulated body phantom, which is not limited in the present disclosure.

In the case the simulation phantom is a simulated head phantom or a simulated head-neck phantom, the simulated normal tissue 100 may include a simulated skull 1, a simulated soft tissue 2 filled within the simulated skull 1, and a simulated skin 4 disposed outside the simulated skull 1. The simulated target volume 3 is disposed within the simulated soft tissue 2, and the simulated skull 1, the simulated soft tissue 2, and the simulated skin 4 at least have the first characteristic or the second characteristic, such that the image of the simulated skull 1, the image of the simulated soft tissue 2 and the image of the simulated skin 4 can be distinguishable on both the first imaging device and the second imaging device. The different structures within the simulated soft tissue 2 may also at least have the first characteristic or the second characteristic, such that the images of the different structures within the simulated soft tissue 2 can also be distinguishable on the first imaging device and the second imaging device. Exemplarily, the different structures within the simulated soft tissue 2 may include the brain, cerebellum, diencephalon, brainstem, etc.

In the case that the simulation phantom is a simulated body phantom, the simulated normal tissue 100 may include a thoracic cavity and an abdominal cavity. Organs such as heart and lungs may be provided within the thoracic cavity, and organs such as stomach, liver, gallbladder, spleen, pancreas, and kidneys may be provided within the abdominal cavity.

In order to provide a more realistic simulation of the patient, the simulation phantom in these embodiments may further include a simulated target volume driving device for driving the simulated target volume to move along a predetermined trajectory at a predetermined frequency. Thus, the simulation phantom may be capable of performing a simulation of the situation in which the tumor target volume is located in the lung of a patient, thereby enabling the simulation of the patient to be more realistic.

Furthermore, the simulated normal tissue in these embodiments may also be provided with a simulation cavity for simulating the internal cavity within the human body, such that the image formed from the simulation phantom can be more similar to the real image of a real human body. In the case that the simulation phantom is a simulated head phantom or a simulated head-neck phantom, the simulation cavity may include a nasal cavity, a maxillary sinus and a respiratory tract.

Described above are merely specific embodiments of the present disclosure, and the protection scope of the present disclosure is not limited thereto. Variations or substitutions easily envisaged by those of ordinary skills in the art within the technical scope of the embodiments of the present disclosure shall all fall within the protection scope of the present disclosure. Therefore, with respect to the protection scope of the present disclosure, the protection scope defined by the claims would prevail.

What is claimed is:

1. A simulation phantom, comprising:

a simulated target volume; and a simulated normal tissue encasing the simulated target volume, wherein the simulated target volume and a portion of the simulated normal tissue abutting the simulated target volume have a first characteristic to enable the simulation phantom to be imaged on a first imaging device, and the simulated target volume and the portion of the simulated normal tissue abutting the simulated target volume further have a second characteristic to enable the simulation phantom to be imaged on a second imaging device different from the first imaging device.

2. The simulation phantom according to claim 1, wherein the first characteristic indicates a difference in CT value and the first imaging device is a CT imaging device; and the second characteristic indicates a difference in hydrogen-containing density and the second imaging device is a magnetic resonance imaging device.

3. The simulation phantom according to claim 1, further comprising a cassette for accommodating the simulated target volume, wherein a cassette recess is provided in the simulated normal tissue at a position corresponding to the cassette, the cassette is capable of being housed in the cassette recess, and is detachably connected with the cassette recess, and the simulated target volume and the cassette have the first characteristic and the second characteristic.

4. The simulation phantom according to claim 3, wherein the simulated normal tissue comprises a first body and a second body that are detachably connected to each other, and the cassette is capable of being housed in or removed from the cassette recess by detaching the first body and the second body.

5. The simulation phantom according to claim 3, wherein a film housing groove for housing a film is provided within the cassette.

6. The simulation phantom according to claim 5, wherein the cassette comprises a first cassette and a second cassette opposite to the first cassette and detachably connected to each other, and the film housing groove is formed between opposite surfaces of the first cassette and the second cassette.

7. The simulation phantom according to claim 6, wherein the first cassette and the second cassette are detachably connected to each other via a locating pin and locating hole that are mutually fitted.

8. The simulation phantom according to claim 3, wherein in a case that the simulation phantom is a simulated head phantom, the cassette is disposed between a back surface and a front surface of the simulated head phantom.

9. The simulation phantom according to claim 3, wherein the cassette is in a cuboid or cube shape.

10. The simulation phantom according to claim 1, wherein the simulated target volume is in a sphere shape.

11. The simulation phantom according to claim 1, wherein a plurality of precisely-marked points for positioning the simulation phantom are provided at an outer surface of the simulated normal tissue.

12. The simulation phantom according to claim 11, wherein in a case that the simulation phantom is a simulated head phantom, the plurality of precisely-marked points comprise a first precisely-marked point, a second precisely-marked point and a third precisely-marked point, wherein the first precisely-marked point is disposed at a forehead of the simulated head phantom; the second precisely-marked point and the third precisely-marked point are respectively disposed at opposite positions of two sides of the forehead of the simulated head phantom; and a center point of the simulated target volume coincides with an intersection between a connecting line connecting the second precisely-marked point and the third precisely-marked point, and a line perpendicular to the connecting line and passing through the first precisely-marked point.

13. The simulation phantom according to claim 11, wherein the precisely-marked points and the outer surface of the simulated normal tissue at least have the first characteristic or the second characteristic.

14. The simulation phantom according to claim 1, wherein a plurality of marked points are provided inside the simulated normal tissue, and the plurality of marked points and portions of the simulated normal tissue abutting the marked points at least have the first characteristic or the second characteristic.

15. The simulation phantom according to claim 14, wherein in a case that the simulation phantom is a simulated head phantom, the plurality of marked points are disposed in a simulated soft tissue of a forehead of the simulated head phantom.

16. The simulation phantom according to claim 1, wherein a spherical hollow cavity is provided in a center of the simulated target volume, and a spherical point of the spherical hollow cavity coincides with a center point of the simulated target volume.

17. The simulation phantom according to claim 1, wherein the simulation phantom is a simulated head phantom, a simulated head-neck phantom or a simulated body phantom.

18. The simulation phantom according to claim 17, wherein in a case that the simulation phantom is the simulated head phantom or the simulated head-neck phantom, the simulated normal tissue comprises a simulated skull, a simulated soft tissue filled within the simulated skull, and a simulated skin disposed outside the simulated skull, and wherein the simulated target volume is disposed within the simulated soft tissue, and the simulated skull, the simulated soft tissue, and the simulated skin at least have the first characteristic or the second characteristic.

19. The simulation phantom according to claim 1, further comprising: a simulated target volume driving device for driving the simulated target volume to move along a predetermined trajectory at a predetermined frequency.

* * * * *